United States Patent
Heiferman

(10) Patent No.: US 11,065,096 B2
(45) Date of Patent: Jul. 20, 2021

(54) THROMBOEMBOLIC PROTECTIVE FLOW-DIVERTING, COMMON CAROTID TO EXTERNAL CAROTID INTRAVASCULAR STENT

(71) Applicant: Loyola University Chicago, Maywood, IL (US)

(72) Inventor: Daniel Heiferman, Westchester, IL (US)

(73) Assignee: Loyola University Chicago, Maywood, IL (US)

( * ) Notice: Subject to any disclaimer, the term of this patent is extended or adjusted under 35 U.S.C. 154(b) by 0 days.

(21) Appl. No.: 15/994,205

(22) Filed: May 31, 2018

(65) Prior Publication Data

US 2019/0110881 A1     Apr. 18, 2019

Related U.S. Application Data

(60) Provisional application No. 62/571,312, filed on Oct. 12, 2017.

(51) Int. Cl.
*A61F 2/06*      (2013.01)
*A61F 2/01*      (2006.01)
(Continued)

(52) U.S. Cl.
CPC .......... *A61F 2/06* (2013.01); *A61B 17/12113* (2013.01); *A61B 17/12136* (2013.01);
(Continued)

(58) Field of Classification Search
CPC .............................. A61F 2/01; A61F 2002/068
See application file for complete search history.

(56) References Cited

U.S. PATENT DOCUMENTS 6,163,721 A    12/2000   Thompson
6,167,303 A    12/2000   Thompson
(Continued)

OTHER PUBLICATIONS

Horst Sievert, Jennifer Franke, Ygael Grad, Boaz Nishri, Yaron Assaf, Ofe Yodfat, Albrecht Romer, Greg C. Robertson, Gregg W. Stone; "A Novel Carotid Device for Embolic Diversion: Lessons Learned from a "First in Man" Trial in Patients with Atrial Fibrillation"; Cardiovasc Intervent Radiol; 2012; 35: 406-412.

(Continued)

*Primary Examiner* — Leslie Lopez
(74) *Attorney, Agent, or Firm* — Hartman Global IP Law; Gary M. Hartman; Domenica N. S. Hartman

(57) ABSTRACT

Medical procedures and devices suitable for reducing the risk of embolic cerebrovascular events, including but not limited to cardioembolic stroke, that result from emboli entering the right or left common carotid artery. The invention uses a combination of intracranial flow diverting stent technologies and carotid stent technologies to achieve clinical objectives of embolic stroke prevention without thromboembolic and/or vascular stenosis complication. Such a stent has struts that generate high radial forces for endothelial apposition, and a mesh with interstices sufficiently small to prevent clinically significant-sized embolic material from passing therethrough from the common carotid artery into the internal carotid artery, but sufficiently large to enable blood and small clinically insignificant-sized embolic material to pass therethrough from the common carotid artery into the internal carotid artery.

17 Claims, 3 Drawing Sheets

(51) Int. Cl.
  *A61F 2/90* (2013.01)
  *A61B 17/12* (2006.01)

(52) U.S. Cl.
  CPC .............. *A61F 2/01* (2013.01); *A61F 2/90* (2013.01); *A61F 2002/018* (2013.01); *A61F 2002/068* (2013.01); *A61F 2230/0006* (2013.01); *A61F 2250/0019* (2013.01); *A61F 2250/0036* (2013.01); *A61F 2250/0039* (2013.01)

(56) References Cited

U.S. PATENT DOCUMENTS

| | | | |
|---|---|---|---|
| 6,185,454 B1 | 2/2001 | Thompson | |
| 7,722,597 B2 | 5/2010 | Plowiecki | |
| 8,509,355 B2 | 8/2013 | Bradley et al. | |
| 8,911,490 B2 | 12/2014 | Perkins et al. | |
| 9,005,270 B2 | 4/2015 | Perkins et al. | |
| 2004/0010308 A1* | 1/2004 | Zafrir-Pachter | A61F 2/82 623/1.35 |
| 2004/0122468 A1 | 6/2004 | Yodfat et al. | |
| 2006/0142836 A1* | 6/2006 | Hartley | A61F 2/95 623/1.11 |
| 2008/0228173 A1 | 9/2008 | Plowiecki | |
| 2015/0305631 A1 | 10/2015 | Lahm et al. | |

OTHER PUBLICATIONS

Yazan J. Alderazi; Dearshan Shastri, Tareq Kass-Hout, Charles J. Prestigiacomo, and Chirag D. Gandhi, "Flow Diverters for Intracranial Aneurysms"; Stroke Research and Treatment; vol. 2014, Article ID 415653, 12 pages.

* cited by examiner

THROMBOEMBOLIC PROTECTIVE FLOW-DIVERTING, COMMON CAROTID TO EXTERNAL CAROTID INTRAVASCULAR STENT

CROSS REFERENCE TO RELATED APPLICATIONS

This application claims the benefit of U.S. Provisional Application No. 62/571,312, filed Oct. 12, 2017, the contents of which are incorporated herein by reference.

BACKGROUND OF THE INVENTION

The present invention generally relates to high radial force stents capable of being placed at the bifurcation of the common carotid artery to inhibit emboli from entering the internal carotid artery, thereby reducing the risk of ischemic stroke.

Ischemic strokes are well-known physiological phenomena in which the blood supply to part of the brain is decreased, leading to dysfunction of the brain tissue in that area. One cause of ischemic strokes is the obstruction of an artery due to an embolus that has traveled to the brain from elsewhere in the body. Because the heart is the most common source of emboli that cause embolic strokes, cardioembolic stroke is of particular interest and will be discussed below, though other systemic embolic sources may also be or become of interest, including non-cardiac embolic stroke, as a nonlimiting example, blood clots from the leg that pass through a patent foramen ovale. Because various aspects of ischemic strokes and embolisms are well known to those of ordinary skill in the art, a further detailed discussion will not be presented here.

In 2015, clinical trials were published that proved the efficacy of mechanical thrombectomy for the treatment of large vessel occlusions causing ischemic stroke. A mechanical thrombectomy involves pulling a blood clot out of a major blood vessel of the brain, through an interventional radiology procedure, to prevent the completion of a stroke that is actively occurring. Since that time, patients are frequently seen with atrial fibrillation who are already being adequately treated with stroke prevention measures, e.g., anticoagulants, but nonetheless, still have a cardioembolic cerebrovascular event. The lives of these patients may be saved if they meet appropriate criteria for undergoing a thrombectomy procedure. Thereafter, the likelihood of the patient suffering another stroke remains high or may increase in light of the fact that the previous stroke prevention measures had failed.

Endovascular neurosurgery is rapidly evolving, with new products and devices continually being introduced and advancements being made with each iteration. In 2011, the FDA approved a device called the Pipeline™ embolization device (Medtronic, USA), which is a braided intracranial stent. This stent is placed over the neck of an aneurysm, and without the need for coils, an aneurysm will thrombose with time. Additionally, any branching vessel that may be covered by the stent will continue to have flow through it. Blood does not flow into areas of high resistance, like the dome of an aneurysm, but will flow where there is low resistance, like a branching vessel with flow demand to tissues.

Most cardioembolic strokes result from emboli entering either the right or left common carotid artery (CCA). The common carotid artery bifurcates in the neck into the internal and external carotid artery (respectively, the ICA and ECA), leading to the brain and the face, respectively. A mesh product referred to as the Diverter™ (MindGuard Ltd, Israel), disclosed in U.S. Patent Application Publication No. 2004/0122468 to Yodfat et al., is a braided mesh "diverting filter" designed to be positioned in the common carotid to external carotid, with the wall of the filter overlying the internal carotid artery. This procedure (referred to as "e-DIRECT") was intended to direct cardioemboli away from the brain to the external carotid circulation, while maintaining flow through the wall of the stent into the protected internal carotid artery. For this purpose, Yodfat et al. teach that, taking into consideration the hemocompatibility and hemodynamical point of view, critical for the fulfillment of safety requirements, the geometry and material composition of the filter were determined to be very low radial and longitudinal forces and rigidity compared to endovascular stents, using tubular braided structure analysis. While the diverting filter disclosed in Yodfat et al. demonstrated its intended goal of preventing embolic stroke in a porcine model, significant complications were encountered with in-stent stenosis and neointimal proliferation in a study with human patients. Yodfat et al. discloses general information concerning the types of conditions and issues intended to be addressed by the diverting filter disclosed therein, procedures for placing the diverting filter, and terminology useful for describing physical characterizations of the diverting filter and similar stent-like devices, and for these reasons Yodfat et al. is incorporated herein by reference.

In view of the above, it can be appreciated that there is an ongoing need for procedures capable of reducing the risk of cardioembolic cerebrovascular events, including but not limited to cardioembolic strokes, and particularly in those who have failed anticoagulation therapy.

BRIEF DESCRIPTION OF THE INVENTION

The present invention provides a medical procedure and device suitable for reducing the risk of embolic cerebrovascular events, including but not limited to cardioembolic stroke, that result from emboli entering the right or left common carotid artery. The invention uses a combination of intracranial flow diverting stent technologies and carotid stent technologies to achieve clinical objectives of embolic stroke prevention without thromboembolic and/or vascular stenosis complication.

According to one aspect of the invention, a medical procedure for reducing the risk of embolic cerebrovascular events includes placing a stent at the bifurcation of the common carotid artery, so that a proximal end of the stent is within the common carotid artery, a distal end of the stent is within the external carotid artery, and a midportion of the stent is located at the origin of the internal carotid artery from the common carotid artery. The stent has struts that generate high radial forces for endothelial apposition, and a braided mesh with interstices sufficiently small to prevent embolic material from passing therethrough from the common carotid artery into the internal carotid artery but sufficiently large to enable blood to pass therethrough from the common carotid artery into the internal carotid artery. In combination the braided mesh and the struts cooperate to create flow dynamics within the lumen of the stent that redirect embolic material entering the lumen away from the origin of the internal carotid artery and into the external carotid artery rather than being filtered or captured by the braided mesh.

Other aspects of the invention include stents configured and adapted to perform a medical procedure comprising the steps described above. Such a stent may be a self-expanding intravascular stent having a tubular body comprising a braided mesh and struts. The braided mesh is formed of filaments defining the interstices, wherein the interstices are sufficiently small to prevent embolic material from passing therethrough but sufficiently large to enable blood to pass therethrough. The struts are arranged as a lattice to create a scaffolding that generates radial forces greater than the braided mesh when the tubular body of the stent is expanded.

Technical aspects of the procedure and stents described above preferably include the ability of the stents to redirect emboli from the internal carotid artery to the external carotid artery while continuously generating sufficiently high radial forces that maintain adequate vessel wall apposition, which promotes long-term stent patency.

Other aspects and advantages of this invention will be further appreciated from the following detailed description.

DETAILED DESCRIPTION OF THE INVENTION

FIGS. 3 through 7B represent embodiments of a self-expanding intravascular stent adapted for use as a thromboembolic flow-diverting device that can be placed in the common and external carotid arteries to divert emboli to the external carotid artery without obstructing blood flow into the internal carotid artery. The stent incorporates struts (tines) arranged to form a scaffolding that increases the radial forces generated by the stent when expanded within the common and external carotid arteries, wherein the radial forces generated by the stent are intentionally sufficient so that the high radial forces against the vessel walls of the common and external carotid arteries allow for adequate endothelial apposition, promoting neoendothelialization over the stent and thus leading to long-term stent patency and limiting the need for long term dual antiplatelet agents. The intravascular stent discussed below may be referred to as a high radial force stent to distinguish it from conventional stents and the Diverter™ diverting filter disclosed in Yodfat et al.

As previously noted, because the heart is the most common source of emboli that cause embolic cerebrovascular events, cardioembolic stroke is of particular interest to the following discussion, though the teachings of the present disclosure can also be applied to embolic cerebrovascular events resulting from other systemic embolic sources.

Figure 2:
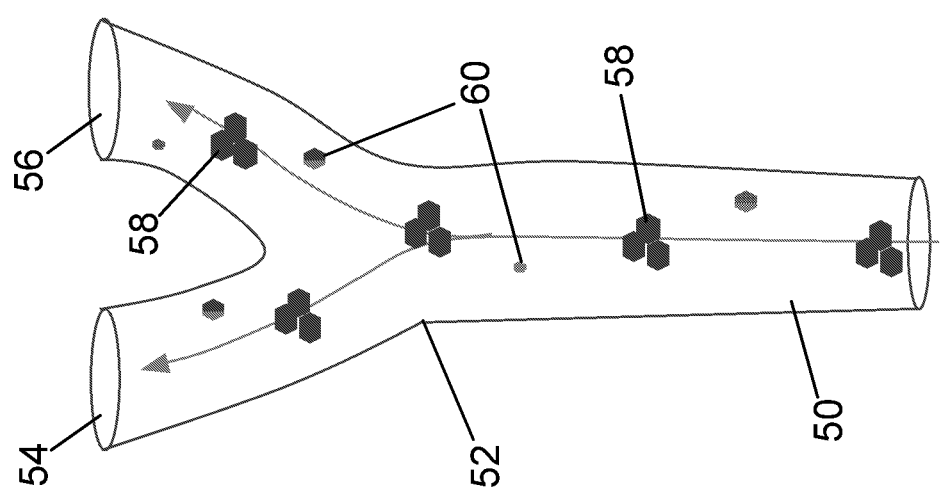
FIG. 2 schematically represents emboli present in the blood flowing from the common carotid artery into the external and internal carotid arteries.
Figure 1:
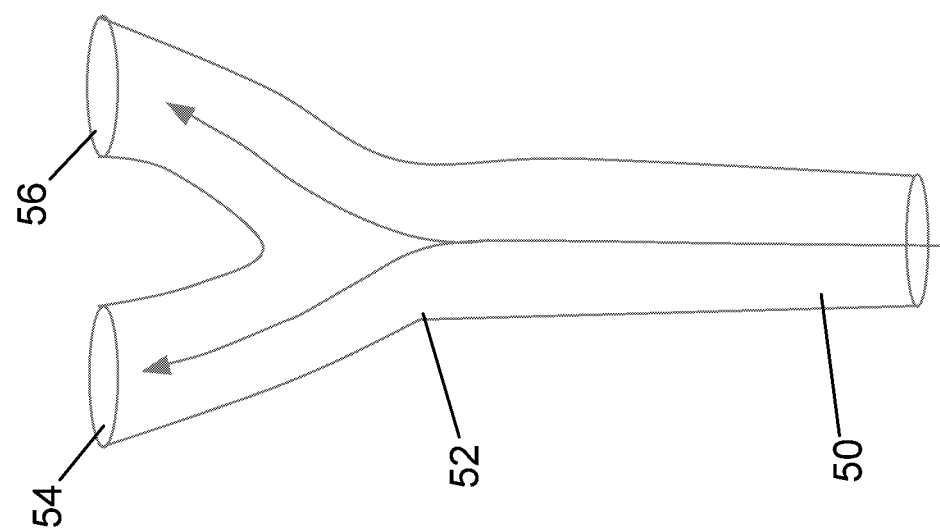
FIG. 1 schematically represents the common carotid artery where it bifurcates into the external and internal carotid arteries, and represents normal blood flow from the common carotid artery into the external and internal carotid arteries.

FIG. 1 schematically represents the bifurcation 52 of the common carotid artery (CCA) 50 leading into the external and internal carotid arteries (ECA and ICA, respectively) 54 and 56. The blood flow represented in FIG. 1 may be referred to as normal, meaning that no obstructions are present in the arteries 50, 54, and 56 and no emboli are present in the blood flow that would pose a risk for an embolic cerebrovascular event, such as an ischemic stroke. FIG. 2 schematically represents the presence of emboli 58 and 60 in the blood flowing into the bifurcation 52, and then into the external and internal carotid arteries 54 and 56. The emboli 58 and 60 flowing into the external carotid artery 54 are asymptomatic, meaning that the presence of the emboli 58 and 60 in the external carotid artery 54 poses no risk of stroke in accordance with knowledge gained from embolizing and/or sacrificing external carotid artery branches for head and neck tumor surgery and refractory bleeding cases. However, if permitted to flow into the internal carotid artery 56, the emboli 58 and 60 and especially relatively large emboli 58 are associated with a risk of stroke, in which case the emboli 58 and possibly also the smaller emboli 60 may be referred to as clinically significant-sized emboli or embolic material. The conventional wisdom regarding the size threshold for embolic material causing a clinical significant cerebral infarct may be drawn from the use of carotid distal embolic protection devices, which comprise an umbrella-like mesh that is placed in the internal carotid artery during carotid stenting procedures for carotid stenosis and then removed at the end of the procedure. The pore size of the meshes of these devices, which include devices available from Boston Scientific Scimed, Inc., under the name FilterWire® EZ and available from the Cordis Corporation under the name AngioGuard®, range from 40 to 150 micrometers. While carotid distal protection devices prevent or significantly reduce stroke during carotid stenting procedures, these devices are intended to capture any clinically significant thromboemboli, and as such if the device were to be kept in place it would become clogged with embolic material over time and potentially cause distal and proximal internal carotid artery thrombosis, resulting in a stroke.

Figure 3:
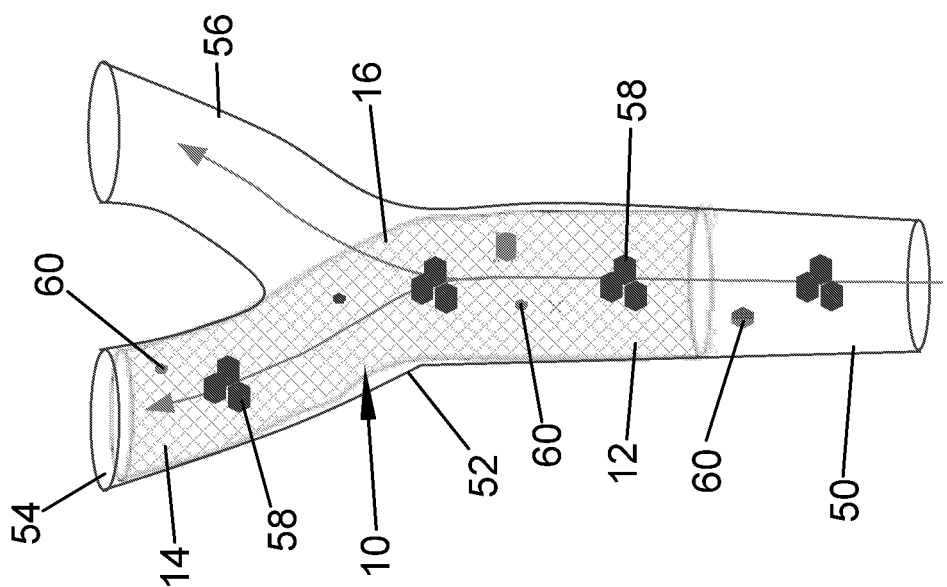
FIG. 3 schematically represents a high radial force stent placed at the bifurcation of the common carotid artery so as to divert emboli to the external carotid artery without obstructing blood flowing into the internal carotid artery in accordance with a nonlimiting embodiment of the invention.

FIG. 3 schematically represents a high radial force stent 10 placed at the bifurcation 52 of the common carotid artery 50 so that a proximal end 12 of the stent 10 is located in the common carotid artery 50, a distal end 14 of the stent 10 is located in the external carotid artery 54, and a midportion 16 of the stent 10 is located at the origin of the internal carotid artery 56 from the common carotid artery 50. The proximal end 12, distal end 14, and midportion 16 therebetween define a tubular body and the stent 10 comprises a lumen 24 defined by and within the tubular body. The midportion 16 of the stent 10 functions as a diverter that is capable of preventing at least some emboli present in the blood flow from entering the internal carotid artery 56, and to instead divert those emboli into the external carotid artery 54 where the emboli pose no risk of ischemic stroke. It will be understood that the high radial force stent 10 does not necessarily prevent all emboli from entering the internal carotid artery 56, but instead is intended to divert clinically significant-sized emboli 58 and 60 that pose a risk of stroke as a result of being of sufficient size to occlude arteries in the brain, as a nonlimiting example, emboli having a cross-sectional dimension on the order of about 500 micrometers and larger, and in some cases as small as about 40 to 150 micrometers. As represented in FIG. 3, the flow dynamics through the stent 10 are such that the relatively larger emboli 58 as well as the relatively smaller emboli 60 are preferably prevented from entering the internal carotid artery 56. However, it is foreseeable that clinically insignificant-sized embolic material could pass through the midportion 16 and enter the internal carotid artery 56. In any event, the stent 10 is not intended to capture embolic material, which over time could result in the internal carotid artery 56 eventually becoming obstructed at the bifurcation 52. As such, the stent 10 functionally differs from the aforementioned carotid distal embolic protection devices. The stent 10 is a fluid dynamic altering flow-diverting stent that is configured to redirect embolic material through the lumen 24 of the stent 10, away from the internal carotid artery 56 rather than filter embolic material out with the stent wall, since the latter would lead to vessel thrombosis as discussed above in reference to the unsuitability of long-term placement of a carotid distal embolic protection device.

Figure 4:
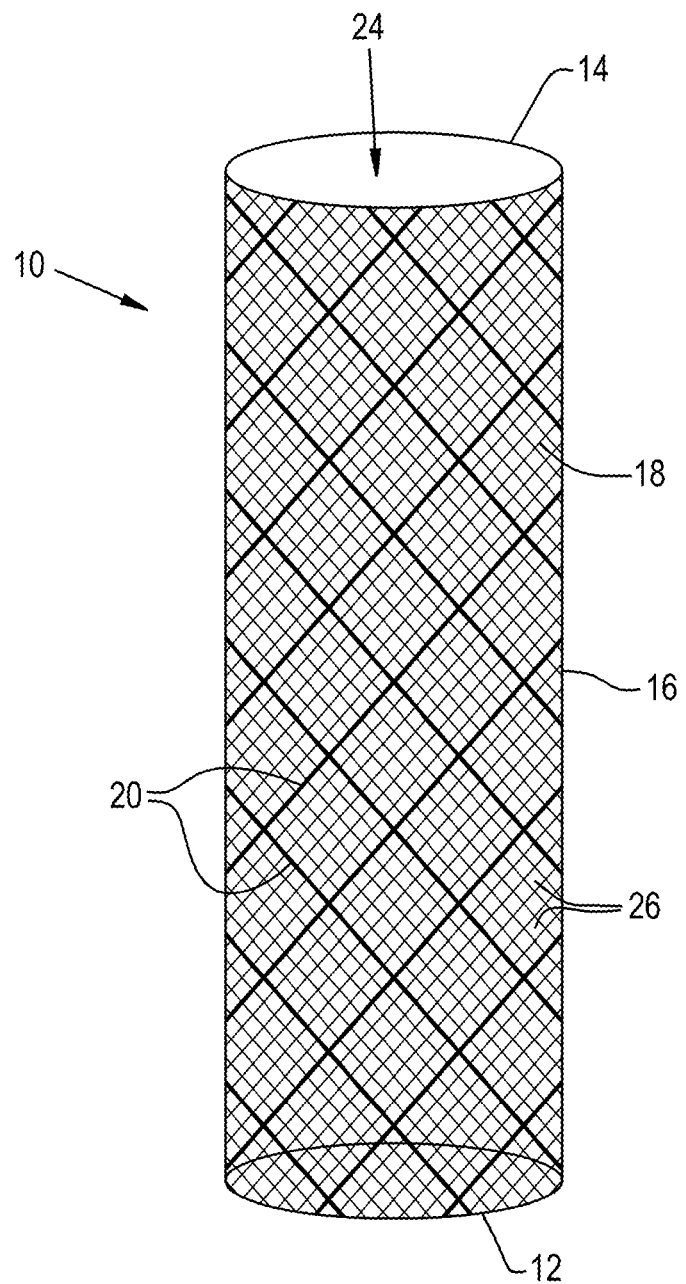
FIG. 4 schematically represents a high radial force stent of a type represented in FIG. 3 and in accordance with a nonlimiting embodiment of the invention.

FIG. 4 schematically represents an embodiment of the high radial force stent 10 and indicates the stent 10 as conventionally having a tubular body comprising a braided mesh 18, but modified to incorporate struts (tines) 20 arranged in the form of a lattice, creating a scaffolding that increases the radial forces generated by the stent 10 when expanded within the common and external carotid arteries 50 and 54. To prevent the passage of clinically significant-sized emboli having cross-sectional dimensions of about 500 micrometers or larger, the mesh 18 of the high radial force stent 10 preferably defines interstices (openings or pores) 26 generally on the order of about 20 to 200 micrometers at their maximum width, which is consistent with pore sizes of typical distal protection devices used in modern carotid stenting procedures. However, it should be appreciated that optimal porosities for a given stent 10 should be evaluated and determined to minimize mesh density while diverting clinically significant-sized embolic material. For purposes of the latter, the mesh 18 may be formed by a high density of braided metallic fibers. Regarding the characteristics of the mesh 18, the stent 10 may be similar to commercially available intracranial flow diverting stent technology that has been developed to treat intracranial aneurysms. As understood in the art, intracranial flow diverting stents are used to treat large intracranial aneurysms by diverting flow away from the aneurysm neck (lumen). Flow diverting stents provide a platform for bridging the aneurysm as a result of thrombosis and obliteration of the aneurysm lumen, and also provide a scaffolding for later neoendothelial proliferation. Notable but nonlimiting examples of intracranial flow diverting stents are commercially available under the names Pipeline™ Flex (Medtronic, Inc.), Silk™ (SFD), and Surpass™ (Stryker Neurovascular). The Pipeline™ stent has been reported as being a 48-strand braided mesh design formed by 75% cobalt chromium/25% platinum tungsten wire, available in diameters ranging from 2.50 to 5.00 mm, lengths ranging from 10 to 35 mm, having an approximately 30 to 35% metal surface area coverage, and having a pore size ostensibly on the order of 20 to 250 micrometers. The Silk™ stent has been reported as being a mesh design formed by a nickel-titanium (Nitinol) alloy with platinum microfilaments, having a 35 to 55% metal surface area coverage, and a pore size of 110 to 250 micrometers. The Surpass™ stent has been reported as being a mesh design formed by cobalt-chromium strands with interwoven platinum/tungsten wires, having a 30% metal surface area coverage, and pore sizes resulting in about 20 to 32 pores/mm². It is believed that a suitable mesh 18 can be fabricated with filaments or strands formed of one or more biocompatible materials, having diameters of about 10 to about 50 micrometers, and braided to define a tubular body having the above-noted interstice (pore) size range of about 20 to about 200 micrometers. However, it is foreseeable that diameters and interstice sizes outside these ranges might also be useful under certain circumstances.

The above-noted intracranial stents are examples of modern flow diverting technology that can be placed in intercranial vessels, which are very delicate and do not tolerate high radial forces, and therefore fundamentally different from the Diverter™ diverting filter of Yodfat et al., which is applied to a different pathology in a different vascular territory. The scaffolding formed by the struts 20 of the stent 10 serve to generate additional radial forces when the stent 10 is expanded within the common and external carotid arteries 50 and 54, well beyond the radial forces generated by the above-noted intracranial flow diverting stents and also beyond radial forces generated by the Diverter™ diverting filter of Yodfat et al., and more in line with the radial forces produced by modern carotid stents used for atherosclerotic disease treatment, including but not limited to carotid stents discussed in Wissgott et al., Experimental Investigation of Modern and Established Carotid Stents," Fortschr Röntgenstr 2014; 186: 157-165. As an example, a suitable radial force normalized for stent length is believed to be about 0.02 to about 0.08 N/mm, though it is foreseeable that radial forces outside this range might also be useful under certain circumstances. For this purpose, at least some but not necessarily all of the struts 20 are required to be capable of generating a high radial force. In other words, in some cases all of the struts 20 generate high radial forces for adequate endothelial apposition. Alternatively, some of the struts 20 may generate high radial forces for adequate endothelial apposition, while other struts 20 may primarily contribute to the function and structural integrity of the stent 10, for example, by promoting its expansion characteristics, maintaining its overall tubular shape, etc. In any case, the struts 20 are intended to ensure that the lumen 24 of the stent 10 defines a uniform flow passageway through the stent 10 whose flow dynamics are such that clinically significant-sized emboli 58 and 60 remain entrained in the blood flow through the lumen 24 and are thereby diverted to the external carotid artery 54. Some or all of the struts 20 may be formed of a drug-eluting material.

Struts 20 dedicated to high radial forces to achieve endothelial apposition are identified as struts 20A in FIGS. 5A, 5B, 6A, 6B, 7A, and 7B, whereas other optional struts 20 identified as struts 20B may primarily contribute to the function and structural integrity of the stent 10. As further represented in FIGS. 5A, 5B, 6A, and 6B, each set of struts 20A and 20B is represented as defining a separate lattice within or attached to the tubular body of the stent 10. The struts 20B generate radial forces that are less than the struts 20A, but higher than the mesh 18, which may be made up of, for example, about 40 to 100 braided thin metallic filaments. In FIGS. 5A, 5B, 6A, 6B, 7A, and 7B, the higher radial force capability of the struts 20A and B is schematically indicated at least in part as being the result of the struts 20A and B being larger in cross-section than the filaments of the mesh 18, though it should be noted that the higher radial forces generated by the struts 20A and B could be partially or entirely attributable to the struts 20A and B being formed of different materials than the filaments. The struts 20A dedicated to higher radial forces are preferably present along the entire length of the stent 10, but are spaced apart so as not to interfere with the emboli-diverting effect desired for the mesh 18 of the stent 10. It is believed that a suitable mesh 18 can be constructed with struts 20 formed of one or more biocompatible materials, including but not limited to nickel titanium (Nitinol) alloys, cobalt-chromium alloys, and/or platinum-tungsten alloys. The high radial force struts 20/20A preferably have diameters of about 20 to about 300 micrometers, for example, about 30 micrometers, whereas any optional lower radial force struts 20B preferably have smaller diameters, for example, about 10 to about 50 micrometers. The struts 20 may further have a surface area coverage of up to about 50%, for example, about 20 to about 50%, and an interstice (pore) size of about 20 to about 200 micrometers, for example, about 50 micrometers. However, it is foreseeable that the struts 20 could have diameters, surface area coverages, and interstice sizes outside these ranges and yet still be effective. Furthermore, the strut density and interstice size may be variable depending on how much the stent 10 expands during placement.

Figure 5A:
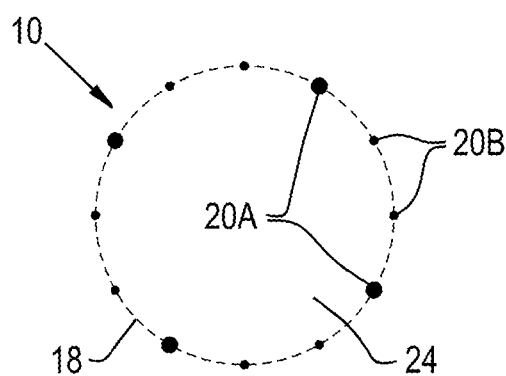
FIGS. 5A, 5B, 6A, 6B, 7A, and 7B schematically represent diametrical cross-sections (FIGS. 5A, 6A, 7A) and longitudinal cross-sections (FIGS. 5B, 6B, 7B) of three nonlimiting embodiments of the high radial force stent of FIG. 4.
Figure 5B:
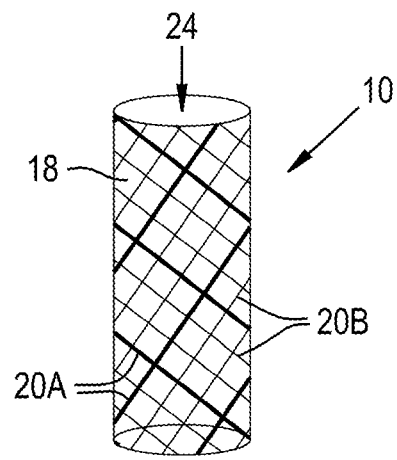
Figure 6A:
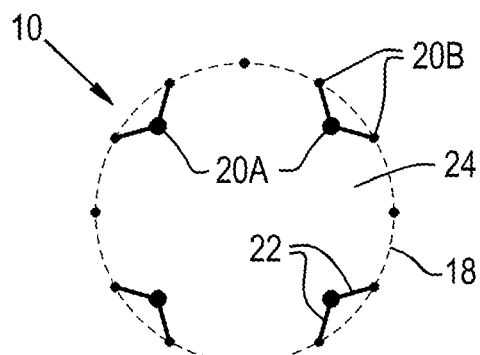
Figure 6B:
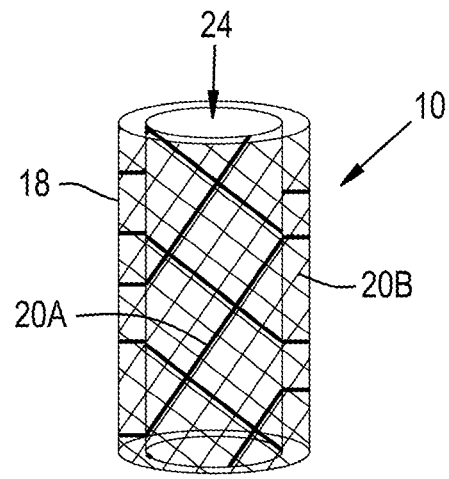
Figure 7A:
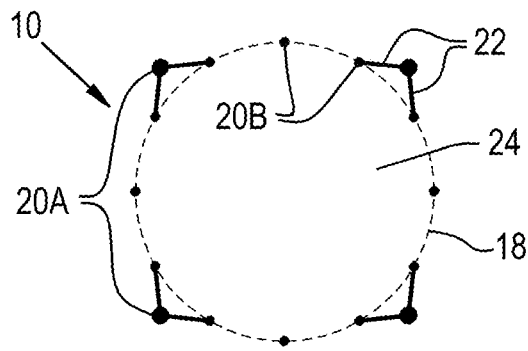
Figure 7B:
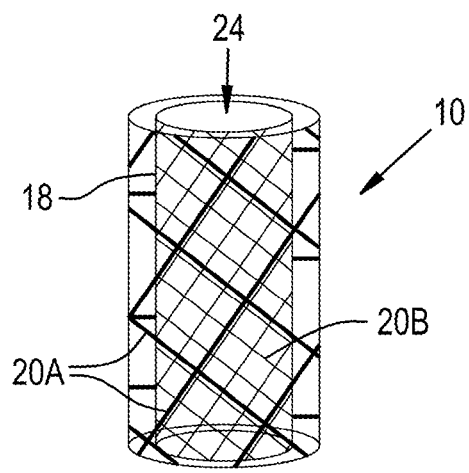

FIGS. 5A and 5B represent a scaffold whose struts 20A (and also the optional struts 20B) lie in the same circular cross-sectional shape defined by the mesh 18, and therefore can be considered to lie entirely within the tubular body of the stent 10. FIGS. 6A, 6B, 7A, and 7B represent scaffolds whose struts 20A lie, respectively, radially interior and exterior of the circular cross-sectional shape of the stent 10 defined by the mesh 18. Because the struts 20A are not in plane with the mesh 18, and therefore are not braided into the mesh 18, the struts 20A are represented as connected to the mesh 18 by tendrils 22. As such, the struts 20A are outside the circular cross-sectional shape defined by the mesh 18, and therefore can be considered to lie entirely outside the tubular body of the stent 10. To facilitate their connection, the tendrils 22 may require attachment to intermediate-sized filaments, i.e., filaments that are larger than the filaments of the mesh 18. As represented in FIGS. 5A, 5B, 6A, 6B, 7A, and 7B,—the struts 20B, shown as braided into the mesh 18, can serve as the required intermediate-sized filaments within the mesh 18. Alternatively, the tendrils 22 may be connected directly to the filaments of the mesh 18, in which case the struts 20B may not be needed for this purpose and, in some cases, could be omitted.

For purposes of placement and deployment from the common carotid to the external carotid artery 54, the stent 10 should be sized to have a pre-deployed diameter within the typical range of inner diameters of standard carotid stent deployment catheters, a post-deployed diameter within the range of normal human common carotid arteries, typically about 7-8 mm, and have a length of about 40-70 mm or greater, though other dimensions are foreseeable and within the scope of the invention. Though not shown, the stent 10 could be formed to have a tapered shape for proper fit in the common and external carotid arteries. For example, the stent 10 could be tapered to the size of a normal human external carotid arteries, typically about 4-5 mm. It should be understood that the stent 10 would be made available in multiple different diameters, lengths, and proximal and distal taper variations in order to meet the needs of patients.

The stent 10 may be placed at the conclusion of or otherwise following an endovascular mechanical thrombectomy stroke treatment or may be performed prophylactically in patients with atrial fibrillation who are at high risk for anticoagulation therapy. The stent 10 can be delivered and deployed using known catheterization procedures. Though the stent 10 is preferably self-expanding, the placement and expansion of the stent 10 may by performed with the assistance of balloon angioplasty. Optical coherence tomography and/or intravascular ultrasound evaluation may be performed to confirm strut-wall apposition. The densities of the meshes of the above-noted intracranial flow diverting stents are known to be altered by lengthening or shortening the stents during deployment, which in turn affects the sizes of their mesh interstices. Consequently, placement of the stent 10 should be performed with appropriate deployment technology. For radiographic visualization, at least some of the struts 20A and/or 20B must be radiopaque throughout the length of the stent 10 to be appropriately angiographically visualizable during deployment. Patients receiving the stent 10 may undergo antiplatelet medication function testing to assess whether they are responders to aspirin, Plavix®, or other antiplatelet medication prior to undergoing stent implantation, or might be switched to an alternative antiplatelet medication regiment. It is foreseeable that patients will benefit from a predetermined course of dual antiplatelet medication therapy, followed by long-term single antiplatelet therapy, as is standard for intravascular stents throughout the body including intracranial, carotid, cardiac, and peripheral.

From the foregoing, it can be appreciated that a notable aspect of the stent 10 is the incorporation of high radial force struts 20/20A into the braided mesh 18, the latter of which can be the same or an equivalent of meshes used in flow diverting stents. The high radial force struts 20/20A allow adequate vessel wall apposition, which promotes long-term stent patency. The high radial force struts 20/20A are particularly intended to address issues with in-stent stenosis, which were reported to result in the failure of human clinical trials carried out with the Diverter™ diverting filter disclosed in Yodfat et al.

While the invention has been described in terms of particular embodiments, it should be apparent that alternatives could be adopted by one skilled in the art. For example, the stents could differ in appearance and construction from the embodiments described herein and shown in the drawings, functions of certain components of the stents could be performed by components of different construction but capable of a similar (though not necessarily equivalent) function, and appropriate materials could be substituted for those noted. As such, it should be understood that the above detailed description is intended to describe the particular embodiments represented in the drawings and certain but not necessarily all features and aspects thereof, and to identify certain but not necessarily all alternatives to the represented embodiments and described features and aspects. As a nonlimiting example, the invention encompasses additional or alternative embodiments in which one or more features or aspects of a disclosed embodiment could be eliminated and/or one or more features or aspects of different disclosed embodiments may be combined. In addition, stents disclosed herein could be integrated with traditional common carotid stents in patients with concomitant cardiogenic source and carotid bifurcation stenosis, in which case the stents might have a Y-shaped configuration, though other configurations are also foreseeable. Accordingly, it should be understood that the invention is not necessarily limited to any embodiment described herein or illustrated in the drawings. It should also be understood that the phraseology and terminology employed above are for the purpose of describing the illustrated embodiments, and do not necessarily serve as limitations to the scope of the invention. Therefore, the scope of the invention is to be limited only by the following claims.

The invention claimed is:

1. A self expanding intravascular stent adapted for use as a thromboembolic flow-diverting device and placement at a bifurcation of a common carotid artery to divert emboli from an origin of an internal carotid artery without obstructing blood flow into the internal carotid artery, the stent having a lumen within and defined by a tubular body having a circular cross-sectional shape, a circumference defined by the circular cross-sectional shape, a proximal end, a distal end, and a length defined by and between the proximal end and the distal end that defines an entire length of the stent, the tubular body comprising:

a braided mesh that defines an entirety of the circular cross-sectional shape of the tubular body, an entirety of the circumference of the tubular body, the lumen of the stent, the proximal end and the distal end of the tubular body, an entirety of the length of the tubular body, the entire length of the stent, a pre-deployed diameter of the tubular body, and a post-deployed diameter of the tubular body, the braided mesh being formed of filaments defining interstices through the tubular body and throughout the entirety of the length of the tubular body and the entire length of the stent, the interstices being sufficiently small to provide an emboli-diverting effect wherein embolic material is prevented from passing therethrough but sufficiently large to enable blood to pass therethrough; and struts arranged as a lattice to create scaffolding along the entirety of the circumference of the tubular body and along the length of the tubular body, the scaffolding generating radial forces greater than radial forces generated by the braided mesh when the tubular body of the stent is expanded to the post-deployed diameter thereof, the struts being spaced apart so as not to interfere with the emboli-diverting effect of the mesh;

wherein in combination the braided mesh and the struts cooperate to create flow dynamics within the lumen of the stent that redirect the embolic material entering the lumen away from the origin of the internal carotid artery and into an external carotid artery rather than being filtered or captured by the braided mesh.

2. The self expanding intravascular stent of claim 1, wherein the interstices of the braided mesh have a maximum width of 20 to 200 micrometers.

3. The self expanding intravascular stent of claim 1, wherein the struts comprise first and second sets of struts, and radial forces generated by the first set of struts are greater than radial forces generated by the second set of struts when the tubular body of the stent is expanded to the post-deployed diameter thereof.

4. The self expanding intravascular stent of claim 3, wherein the first and the second sets of struts define separate first and second lattices within or attached to the braided mesh.

5. The self expanding intravascular stent of claim 3, wherein the radial forces generated by the second set of struts are greater than the radial forces generated by the braided mesh when the tubular body of the stent is expanded to the post-deployed diameter thereof.

6. The self expanding intravascular stent of claim 1, wherein radial forces generated by each of the struts are greater than radial forces generated by the filaments of the braided mesh when the tubular body of the stent is expanded to the post-deployed diameter thereof.

7. The self expanding intravascular stent of claim 1, wherein the struts are larger in cross-section than the filaments of the braided mesh.

8. The self expanding intravascular stent of claim 1, wherein the struts and the filaments of the braided mesh are formed of different biocompatible materials.

9. The self expanding intravascular stent of claim 1, wherein the scaffolding defined by the struts is throughout the entirety of the length of the tubular body and along the entire length of the stent.

10. The self expanding intravascular stent of claim 1, wherein the scaffolding defined by the struts has a circular cross-sectional shape and with the braided mesh defines the pre-deployed diameter and the post-deployed diameter of the tubular body of the stent.

11. The self expanding intravascular stent of claim 1, wherein the scaffolding defined by the struts is radially exterior of the pre-deployed diameter and the post-deployed diameter of the tubular body of the stent.

12. The self expanding intravascular stent of claim 1, wherein the scaffolding defined by the struts is radially interior of the pre-deployed diameter and the post-deployed diameter defined by the braided mesh of the tubular body of the stent.

13. The self expanding intravascular stent of claim 12, wherein the struts are connected to the braided mesh by tendrils.

14. The self expanding intravascular stent of claim 11, wherein the struts are connected to the braided mesh by tendrils.

15. The self expanding intravascular stent of claim 1, wherein the pre-deployed diameter is within a range of inner diameters of standard carotid stent deployment catheters.

16. The self expanding intravascular stent of claim 1, wherein the post-deployed diameter is 7-8 mm.

17. The self expanding intravascular stent of claim 1, wherein the entire length of the stent is 40-70 mm.

\* \* \* \* \*